United States Patent [19]

Ireland

[11] Patent Number: 5,405,859
[45] Date of Patent: Apr. 11, 1995

[54] PATELLAZOLE

[75] Inventor: Chris M. Ireland, Sandy, Utah

[73] Assignee: University of Utah Research Foundation, Salt Lake City, Utah

[21] Appl. No.: 108,829

[22] Filed: Aug. 18, 1993

Related U.S. Application Data

[63] Continuation of Ser. No. 871,583, Apr. 20, 1992, abandoned, which is a continuation of Ser. No. 702,354, May 15, 1991, abandoned, which is a continuation of Ser. No. 383,739, Jul. 21, 1989, abandoned.

[51] Int. Cl.$^6$ ................. C07D 417/14; A61K 31/425
[52] U.S. Cl. .................................... 514/365; 548/204
[58] Field of Search .......................... 548/204; 514/365

[56] References Cited

U.S. PATENT DOCUMENTS

| 2,823,203 | 2/1958 | Clark | 504/36 |
| 4,493,796 | 1/1985 | Rinehart | 504/36 |
| 4,548,814 | 10/1985 | Rinehart | 504/36 |
| 4,631,149 | 12/1986 | Rinehart | 504/36 |
| 4,737,510 | 4/1988 | Rinehart | 504/36 |

OTHER PUBLICATIONS

Zabriskie, JACS 110 7919 (1988).
Corley JACS 110 7920 (1988).
Sessin, et al., "The Chemistry of Lissoclinum Patella", 95 Bull. Soc. Chim. Belg. 20, 9–10, pp. 853–867 (1986).

*Primary Examiner*—Robert Gerstl
*Attorney, Agent, or Firm*—Trask, Britt & Rossa

[57] ABSTRACT

Cytotoxic, antifungal macrolides identified as a patellazoles having a pendant thiazole-epoxy group have been derived from a *Lissoclinum patella* located in the Fiji Islands.

8 Claims, No Drawings

PATELLAZOLE

Licensing Rights: This invention was made with U.S. Government support in the form of NIH grant(s) CA36622 and CA01779. The government may have certain rights in the invention.

This application is a continuation of application Ser. No. 07/871,583, filed Apr. 20, 1992, now abandoned, which was a continuation of application 07/702,354, filed May 15, 1992, now abandoned, which was a continuation of 07/383,739, filed Jul. 21, 1989, now abandoned.

BACKGROUND OF THE INVENTION

Field

This invention relates to cytotoxic macrolides and the process for producing same from naturally occurring organisms such as *Lissoclinum patella*.

State of the Art

Interest in macrolides isolated from various naturally occurring organisms has been widespread. One group of organisms, the tunicates (commonly called sea squirts), has elicited extensive investigation. The chemistry of tunicates was reviewed by Faulkner, 1 *Nat. Prod, Rep.* 551 (1984).

The tunicates have been known to concentrate transition metals and have had isolated therefrom metabolites such as simple amines and complex peptides.

In 1986 Sesin, Gaskell and Ireland, the latter being the inventor of the instant invention, reported in 95 *Bull Soc. Chem. Belg.* 20 9–10, p.853 et seq. (1986) a description of the didemnid tunicate *Lissoclinum patella.* collected in Palau, and a family of unique, cytotoxic cyclic peptides containing thiazole amino acids within the cyclic structures which were produced from said *L. patella*.

DESCRIPTION OF THE INVENTION

An unique group of patellazoles having a pendant thiazole-epoxy group has been produced from a *Lissoclinum patella* located in the Fiji Islands. These patellazoles have potent cytotoxic and antifungal activity.

A *Lissoclinum patella* collected from the Figi Islands was directly screened for cytotoxic and antifungal activity. Minor cytotoxic and antiviral activity was observed.

Samples of *L. patella* were collected from various locations in the Fiji Islands. These were collected from the south side from Ndravuni Island, from Navala Pass off the coast of Viti Levu and from a reef northwest of Yageta Island. These locations all yielded *L. patella* of exactly the same type and yielded the same patellazole compounds when processed as indicated hereinafter.

The *L. patella* a collected from the Fiji Islands are physically indistinguishable from those collected in Palau. However, the Fiji *L. patella* do not yield amino acid compounds upon extraction nor do the Palau *L. patella* yield patellazoles. Upon processing, a simple test to determine the presence of an epoxide group may be used to readily distinguish between the *L. patella* useful in this invention and the *L. patella* which yield amino acids.

Samples of the *L. patella* from the Fiji Islands were pulverized and subjected to various extraction techniques, which resulted in a novel group of macrolides identified as patellazoles because of their derivation from *L. patella* and the presence of a pendant thiazole-epoxy group. These patellazoles have been assigned the following structure:

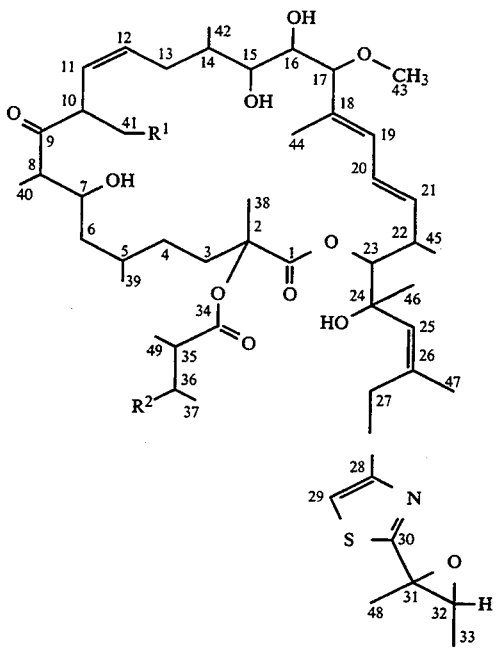

Patellazole A has the depicted structure wherein $R_1$ and $R_2$ are both hydrogen, while patellazole B has the structure wherein $R_1$ is hydrogen and $R_2$ is a hydroxyl group. Patellazole C has the structure wherein $R_1$ and $R_2$ are both hydroxyl groups. All three of these patellazoles have demonstrated potent cytotoxic activity.

A 220 gram sample of *Lissoclinum patella* was freeze dried and pulverized. The pulverized material was subjected to extraction by methyl alcohol (MeOH). The methyl alcohol mixture was further extracted with carbon tetrachloride ($CCl_4$). Gravity column chromatography of this fraction on a silica gel 62 bed followed by successive RD and silica gel HPLC afforded 97 mg of patellazole A, 143 mg of patellazole B and 313 mg of patellazole C.

Patellazole C (3): $[\alpha]_D$ $-100°$ (c 1.06, $CH_2Cl_2$); UV (MeOH) max 241 nm (e26,000); IR (neat) max 3474, 1728, 1708$cm^{-1}$ was assigned molecular formula $C_{49}H_{77}NO_{13}S$ by FABMS mass measurement of the $MH^+$ion (920.5179; requires 920.5197). All forty nine carbons were visible in the $^{13}C$ NMR spectrum (Table 1), and DEPT experiments established the presence of 71 carbon bound protons (13 methyls, 6 methylenes and 20 methines); $D_2O$ exchange FABMS and $^1H$ NMR experiments indicated the presence of six active protons.

A double quantum filtered phase sensitive COSY and a $^1H$-$^{13}C$ chemical shift correlation experiment established all one bond $^1H$-$^{13}C$ connectivities and partial structures representing C3–C8, C10–C15, C16–C17, C18–C23, C25–C26, C32–C33, and C35–C37. The presence and position of an epoxy thiazole was indicated by NMR data (Table I) which compared favorably with 2-t-butyl-4-methylthiazole. The $J_{CH}$ of 186.7 Hz for C29 is consistent with published data for thiazoles. Similarly, the $J_{CH}$ of 72.6 for C32 is indicative of a small ring heterocycle. These assignments were confirmed by treatment of patellazole C with $O_3$ in $CH_2Cl_2$ followed by a reductive workup to give thiazole 4. These partial structures plus three carbonyls account for all sp² atoms indicating the remaining unsaturation must be a ring.

The connection of partial structures in 3 was established by a combination of INAPT, COLOC and 2D INADEQUATE NMR experiments (Table 1). INAPT connections from H3 and H38 to C1 and C2 plus INADEQUATE connection C38-C2-C3 confirmed placement of the ester carbonyl at 171.36 ppm as C1. Irradiation of H8 and H10 gave a signal at 216.43 ppm in the INAPT indicating that C9 is a ketone and extended the carbon chain to C15. Although H15 failed to show vicinal coupling to H16, H17 showed connections to C15 in the INAPT and to C16 in the COLOC. The O-methyl exhibited an INAPT connection to C17 and both H15 and H16 sharpened in the D20 exchange 1H NMR spectrum, indicating that C15 and C16 bear secondary hydroxyls and C17 a methoxyl. Furthermore, the INADEQUATE data showed clear evidence for the sequence C15-C16-C17-C18, which effectively extends the carbon chain to C23. Both the COLOC and INAPT data showed strong correlation of H23 to the ester carbonyl at 171.36 ppm which was previously shown to be C1. This connection establishes a 24 membered macrolide. The proton on C23 showed further INAPT correlations to C24, C25 and C46, and H25 and H46 correlated to C24 in the COLOC. The remainder of the side chain was also established from long range correlation data and was confirmed by isolation of 4. Protons 35 and 49 correlated to the remaining carbonyl at 175.39 ppm confirming the presence of an α-methyl-β-hydroxyl butyrate. The ester was attached at C2 based on deuterium exchange ¹³C NMR studies in which C7, C15, C16, C24 and C36 all exhibited upfield isotope induced shifts from 0.10 to 0.17 ppm, whereas C2, C17 and C23 showed negligible changes. This assignment was also substantiated by ¹H NMR data.

TABLE I

| C no. | 13$C^a$ ppm (mult)$^b$ | | 1H$^c$ ppm (mult, J (Hz)) |
|---|---|---|---|
| Patellazole A: ¹H and ¹³C NMR Data | | | |
| 1 | 172.00 (s) | | |
| 2 | 80.75 (s) | | |
| 3 | 32.37 (t) | A | 1.70 (m) |
| | | B | 2.63 (dt, 13.2, 5.9) |
| 4 | 32.15 (t) | A | 1.02 (m) |
| | | B | 1.25 (m) |
| 5 | 28.46 (d) | | 1.68 (m) |
| 6 | 44.25 (t) | A | 1.20 (m) |
| | | B | 1.59 (m) |
| 7 | 73.33 (d) | | 3.88 (bm) |
| 8 | 48.75 (d) | | 3.25 (dq, 9.5, 6.8) |
| 9 | 214.11 (s) | | |
| 10 | 48.62 (d) | | 4.13 (dq, 10.7, 6.6) |
| 11 | 130.61 (d) | | 5.28 (dd, 10.7, 10.7) |
| 12 | 131.72 (d) | | 5.84 (dt, 10.7, 6.1) |
| 13 | 33.33 (t) | A | 1.60 (m) |
| | | B | 3.53 (dd, 11.9, 11.9) |
| 14 | 38.90 (d) | | 2.08 (m) |
| 15 | 74.91 (d) | | 3.69 (bm) |
| 16 | 69.30 (d) | | 3.85 (dd, 8.3, 2.5) |
| 17 | 88.19 (d) | | 4.00 (d, 8.3) |
| 18 | 132.45 (s) | | |
| 19 | 132.63 (d) | | 6.32 (d, 10.8) |
| 20 | 125.87 (d) | | 6.66 (dd, 15.3, 10.8) |
| 21 | 136.51 (d) | | 6.41 (dd, 15.3, 5.7) |
| 22 | 36.12 (d) | | 3.25 (m) |
| 23 | 85.85 (d) | | 4.92 (bs) |
| 24 | 75.82 (s) | | |
| 25 | 131.93 (d) | | 5.34 (s) |
| 26 | 133.18 (s) | | |
| 27 | 34.74 (t) | A | 3.15 (d, 13.7) |
| | | B | 4.11 (d, 13.7) |
| 28 | 154.27 (s) | | |
| 29 | 114.66 (d) | | 6.20 (s) |
| 30 | 174.78 (s) | | |
| 31 | 60.56 (s) | | |
| 32 | 65.93 (d) | | 2.69 (q, 5.4) |
| 33 | 14.17 (q) | | 0.93 (d, 5.4) |
| 34 | 175.64 (s) | | |
| 35 | 41.73 (d) | | 2.31 (dq, 13.6, 7.0) |
| 36 | 27.02 (t) | A | 1.35 (m) |
| | | B | 1.72 (dq, 13.6, 7.3) |
| 37 | 12.00 (q) | | 0.90 (t, 7.3) |
| 38 | 24.01 (q) | | 1.45 (s) |
| 39 | 18.38 (q) | | 0.71 (d, 6.4) |
| 40 | 14.09 (q) | | 0.89 (d, 6.8) |
| 41 | 15.35 (q) | | 1.32 (d, 6.6) |
| 42 | 16.14 (q) | | 1.01 (d, 6.6) |
| 43 | 56.28 (q) | | 3.17 (s) |
| 44 | 11.42 (q) | | 1.97 (s) |
| 45 | 19.22 (q) | | 1.59 (d, 7.0) |
| 46 | 27.30 (q) | | 1.44 (s) |
| 47 | 24.75 (q) | | 1.54 (s) |
| 48 | 16.08 (q) | | 1.79 (s) |
| 49 | 17.22 (q) | | 1.17 (d, 7.0) |
| Patellazole B: ¹H and ¹³C NMR Data | | | |
| 1 | 171.95 (s) | | |
| 2 | 81.36 (s) | | |
| 3 | 32.43 (t) | A | 1.83 (dt, 13.4, 4.6) |
| | | B | 2.60 (dt, 13.4, 4.6) |
| 4 | 32.34 (t) | A | 1.00 (dq, 13.4, 3.5) |
| | | B | 1.42 (m) |
| 5 | 28.61 (d) | | 1.73 (bm) |
| 6 | 44.52 (t) | A | 1.28 (ddd, 13.8, 12.0, 2.3) |
| | | B | 1.55 (m) |
| 7 | 73.03 (d) | | 3.88 (m) |
| 8 | 48.97 (d) | | 3.25 (m) |
| 9 | 214.57 (s) | | |
| 10 | 48.54 (d) | | 4.09 (dq, 10.7, 6.7) |
| 11 | 130.63 (d) | | 5.29 (dd, 10.7, 10.7) |
| 12 | 131.67 (d) | | 5.86 (dt, 10.7, 5.5) |
| 13 | 32.91 (t) | A | 1.52 (m) |
| | | B | 3.57 (dd, 12.1, 12.1) |
| 14 | 38.96 (d) | | 2.00 (m) |
| 15 | 74.76 (d) | | 3.67 (bd, 9.3) |
| 16 | 69.69 (d) | | 3.91 (bd, 8.8) |
| 17 | 87.51 (d) | | 4.09 (d, 8.8) |
| 18 | 132.57 (s) | | |
| 19 | 133.55 (d) | | 6.38 (d, 10.8) |
| 20 | 125.59 (d) | | 6.62 (dd, 15.3, 10.8) |
| 21 | 136.59 (d) | | 6.35 (dd, 15.3, 5.6) |
| 22 | 35.87 (d) | | 3.30 (m) |
| 23 | 86.23 (d) | | 4.82 (d, 2.1) |
| 24 | 75.70 (s) | | |
| 25 | 131.14 (d) | | 5.37 (s) |
| 26 | 133.82 (s) | | |
| 27 | 34.85 (t) | A | 3.37 (d, 13.4) |
| | | B | 3.94 (d, 13.4) |
| 28 | 154.29 (s) | | |
| 29 | 114.62 (d) | | 6.22 (s) |
| 30 | 174.99 (s) | | |
| 31 | 60.33 (s) | | |
| 32 | 65.55 (d) | | 2.71 (q, 5.5) |
| 33 | 14.19 (q) | | 0.90 (d, 5.5) |
| 34 | 175.73 (s) | | |
| 35 | 49.66 (d) | | 2.49 (dq, 8.5, 7.1) |
| 36 | 69.62 (d) | | 3.85 (m) |
| 37 | 20.54 (q) | | 1.10 (d, 6.5) |
| 38 | 24.38 (q) | | 1.46 (s) |
| 39 | 18.33 (q) | | 0.72 (d, 6.6) |
| 40 | 13.92 (q) | | 0.83 (d, 6.7) |
| 41 | 15.50 (q) | | 1.33 (d, 6.7) |
| 42 | 16.13 (q) | | 1.11 (d, 7.0) |
| 43 | 56.24 (q) | | 3.22 (s) |
| 44 | 11.18 (q) | | 2.00 (s) |
| 45 | 19.10 (q) | | 1.55 (d, 7.4) |
| 46 | 27.42 (q) | | 1.44 (s) |
| 47 | 24.86 (q) | | 1.57 (bs) |
| 48 | 15.98 (q) | | 1.75 (s) |
| 49 | 14.94 (q) | | 1.09 (d, 7.1) |
| Patellazole C: H and ¹³C NMR Data | | | |
| 1 | 171.36 (s) | | |

TABLE I-continued
IDENTIFICATION OF PATELIAZOLES

| C no. | $^{13}C^a$ ppm (mult)$^b$ | | $^1H^c$ ppm (mult, J (Hz)) |
|---|---|---|---|
| 2 | 81.25 (s) | | |
| 3 | 32.65 (t) | A | 1.90 (bdd, 13.6, 4.4) |
|   |           | B | 2.62 (dd, 13.6, 4.4) |
| 4 | 32.14 (t) | A | 1.06 (m) |
|   |           | B | 1.44 (m) |
| 5 | 28.17 (d) | | 1.85 (bm) |
| 6 | 44.32 (t) | A | 1.30 (ddd, 11.3, 11.3, 2.3) |
|   |           | B | 1.56 (dd, 11.3, 5.7) |
| 7 | 72.56 (d) | | 3.87 (bm) |
| 8 | 50.05 (d) | | 3.13 (dq, 9.5, 6.8) |
| 9 | 216.43 (s) | | |
| 10 | 56.28 (d) | | 4.28 (ddd, 10.8, 7.6, 4.0) |
| 11 | 124.85 (d) | | 5.22 (dd, 10.8, 10.8) |
| 12 | 134.39 (d) | | 5.93 (dt, 10.8, 5.7) |
| 13 | 32.37 (t) | A | 1.53 (m) |
|    |           | B | 3.48 (dd, 12.1, 12.1) |
| 14 | 38.86 (d) | | 1.95 (m) |
| 15 | 74.32 (d) | | 3.68 (bd, 9.7) |
| 16 | 69.44 (d) | | 3.90 (bd, 8.6) |
| 17 | 87.01 (d) | | 4.09 (d, 8.6) |
| 18 | 132.15 (s) | | |
| 19 | 133.36 (d) | | 6.38 (d, 10.8) |
| 20 | 125.31 (d) | | 6.62 (dd, 15.3, 10.8) |
| 21 | 136.14 (d) | | 6.30 (dd, 15.3, 5.6) |
| 22 | 35.69 (d) | | 3.25 (m) |
| 23 | 85.62 (d) | | 4.87 (d, 2.3) |
| 24 | 75.38 (s) | | |
| 25 | 130.40 (d) | | 5.47 (s) |
| 26 | 133.96 (s) | | |
| 27 | 34.68 (t) | A | 3.52 (d, 13.4) |
|    |           | B | 3.83 (d, 13.4) |
| 28 | 154.05 (s) | | |
| 29 | 114.21 (d) | | 6.26 (s) |
| 30 | 174.76 (s) | | |
| 31 | 59.98 (s) | | |
| 32 | 65.00 (d) | | 2.73 (q, 5.4) |
| 33 | 14.03 (q) | | 0.92 (d, 5.4) |
| 34 | 175.39 (s) | | |
| 35 | 49.49 (d) | | 2.51 (dq, 9.0, 7.1) |
| 36 | 69.29 (d) | | 3.85 (m) |
| 37 | 20.36 (q) | | 1.11 (d, 6.5) |
| 38 | 24.20 (q) | | 1.49 (s) |
| 39 | 18.13 (q) | | 0.93 (d, 6.8) |
| 40 | 13.52 (q) | | 0.82 (d, 6.8) |
| 41 | 62.52 (t) | A | 3.77 (dd, 10.8, 4.0) |
|    |           | B | 4.05 (bdd, 10.8, 7.6) |
| 42 | 16.03 (q) | | 1.12 (d, 7.1) |
| 43 | 56.01 (q) | | 3.26 (s) |
| 44 | 10.99 (q) | | 2.00 (s) |
| 45 | 19.08 (q) | | 1.60 (d, 7.1) |
| 46 | 27.49 (q) | | 1.47 (s) |
| 47 | 24.79 (q) | | 1.62 (fd, 1.1) |
| 48 | 15.58 (q) | | 1.67 (s) |
| 49 | 14.85 (q) | | 1.12 (d, 7.1) |

The presence of patellazoles A, B and C in *L. patella* in their precise form as identified herein has not been confirmed. If such patellazoles are, per se, naturally present in *L. patella* they are present in very minor amounts in an impure form, i.e. admixed or combined with a myriad of other organic compounds of various size, structure and properties also present in L. patella.

The cytotoxic and antifungal activity of untreated, unmodified *L. patella* is very minor in comparison with patellazole C, for example. The pure patellazoles free of other chemicals found in *L. patella* have cytotoxic properties which differ very substantially, i.e. more than a matter of degree, from the cytotoxic behavior of *L. patella*.

The following Examples illustrate comparison of the cytotoxic behavior of various patellazoles:

EXAMPLE I

A mixture of patellazole compounds A, B, C was screened for activity. The screening was as follows:

TABLE II

| | In vitro screen (mµ/ml) | | | |
|---|---|---|---|---|
| VIR | ID50 | CELL | MTC | TI |
| VSV | 2.63 | VERO | 100.00 | 38.0 |
| JE | NOT ACT | VERO | 100.00 | NOT ACT |
| YF | NOT ACT | MK2 | 10.00 | NOT ACT |
| RVF | NOT ACT | VERO | 100.00 | NOT ACT |
| PIC | 18.60 | VERO | 100.00 | 5.4 |
| SF | NOT ACT | VERO | 100.00 | NOT ACT |
| VEE | 4.90 | VERO | 100.00 | 20.4 |

The mixture was soluble in methyl alcohol, dimethyl sulfoxide and trichloro methane.

Table II sets forth in intro antiviral test results for a mixture of patellazoles. VSV=vesticular stomatitis virus; JE=Japanese encephalitis; YF=yellow fever; RVF=rift valley fever; PIC=pichinde; SF=sandfly fever; VEE=Venezuelan equine encephalitis.

A crude sample of *L. patella* which was merely ground and untreated chemically showed very minor antifungal and antiviral activity in comparison with the extracted admixture of Patellazoles A, B and C.

EXAMPLE II

Substantially pure compounds of Patellazole B and C were screened for activity. These extracts from a marine tunicate (*L. patella*) were submitted for antiviral testing. Both extracts showed activity against herpes viruses HSV-1 and HSV-2 at concentrations which were not toxic for the host cells (Vero). Patellazole B exhibited significantly more potent antiviral activity against these herpes viruses than Patellazole C.

TABLE III

| | HSV-L | HSV-2 | Cytotoxicity Vero) |
|---|---|---|---|
| Patellazole B | 0.0005 µg/ml | 0.06 µg/ml | 0.75 µg/ml |
| Patellazole C | 0.30 µg/ml | 0.80 µg/ml | 4.0 µg/ml |

An initial screening has shown the relative activities of the patellazoles to be:

A>B>C

Patellazole C is generally more abundant in *L. patella* than Patellazoles A and B, although it is generally less active. Representative screening results are set forth in Table III.

EXAMPLE III

Patellazoles A, B and C were screened against a standard group of cancer cells. Their respective activities are listed in the following tables:

TABLE IV

| | Patellazole A |
|---|---|
| CELL | LOGIC50(W) |
| *LEUK* | |
| MOLT-4 | −4.1 . |
| HL-60 | −3.9 . |
| *PS* | |
| P388 | −4 |
| *RESISTL* | |
| P388/AD | −3.9 . |
| *NSCLC* | |

TABLE IV-continued

Patellazole A

| CELL | LOGIC50(W) |
|---|---|
| SK-MES1 | <−4.5. |
| H460 | −4.4. |
| H520 | −3.1. |
| H322 | −3.9. |
| EKV-X | −4.1. |
| *SCLC* | |
| *COLON* | |
| SW620 | −4. |
| LOVO | −4.1. |
| HT29 | <−4.5. |
| *BREAST* | |
| MCF-7 | −3.9 |
| *RESISTB* | |
| MCF-7/A | −3.3. |
| *CNS* | |
| TE-671 | <−4.5. |
| U-251 | <−4.5. |
| SNB-19 | −4.1. |
| SNB-75 | −2.2. |
| *MELANOMA* | |
| SK-MEL5 | −3.8. |
| *OVARIAN* | |
| A2780 | −4.4. |
| OVCAR-8 | −4. |
| OVCAR-5 | −4.3. |
| OVCAR-4 | −4. |
| *RENAL* | |
| A498 | −4.2. |
| A704 | −4. |
| SN-12KI | <−4.5. |
| UO-31 | −3.9. |
| *PROSTATE* | |
| .AV.LOG IC50 | −4.01 |
| .DELTA | 0.5 |
| .RANGE | 2.3 |

TABLE V

Patellazole B

| CELL | LOGIC50(W) |
|---|---|
| *LEUK* | |
| MOLT-4 | <−4.5. |
| *PS* | |
| P388 | <−4.5. |
| *RESISTL* | |
| P388/AD | <−4.5. |
| *NSCLC* | |
| SK-MES1 | <−4.5. |
| H460 | <−4.5. |
| H322 | <−4.5. |
| A549 | <−4.5. |
| EKV-X | <−4.5. |
| *SCLC* | |
| *COLON* | |
| SW620 | <−4.5. |
| LOVO | <−4.5. |
| HT29 | <−4.5. |
| *BREAST* | |
| MCF-7 | <−4.5 |
| *RESISTB* | |
| MCF-7/A | <−4.5. |
| *CNS* | |
| TE-671 | <−4.5. |
| U-251 | <−4.5. |
| SNB-19 | <−4.5. |
| SNB-44 | <−4.5. |
| SNB-75 | <−4.5. |
| *MELANOMA* | |
| SK-MEL5 | <−4.5. |
| LOX | <−4.5 |
| *OVARIAN* | |
| A2780 | <−4.5. |
| OVCAR-5 | <−4.5. |

TABLE V-continued

Patellazole B

| CELL | LOGIC50(W) |
|---|---|
| OVCAR-4 | <−4.5. |
| *RENAL* | |
| A498 | <−4.5. |
| A704 | <−4.5. |
| SN-12KI | <−4.5. |
| UO-31 | <−4.5. |
| *PROSTATE* | |
| .AV.LOG IC50 | −4.5 |
| .DELTA | 0. |
| .RANGE | 0 |

TABLE VI

Patellazole C

| CELL | LOGIC50(W) |
|---|---|
| *LEUK* | |
| MOLT-4 | −2.1. |
| *PS* | |
| P388 | −1.9. |
| *RESISTL* | |
| *NSCLC* | |
| SK-MES1 | −2.1. |
| H460 | −2.1. |
| A322 | −2.1. |
| EKV-X | −2.. |
| *SCLC* | |
| *COLON* | |
| LOVO | −2.2. |
| HT29 | −3.. |
| *BREAST* | |
| *RESISTB* | |
| MCF-7/A | >−0.5. |
| *CNS* | |
| TE-671 | −2.1. |
| U-251 | −2.1. |
| SNB-19 | −2.. |
| SNB-75 | >−1.5. |
| *MELANOMA* | |
| SK-MEL5 | −1.9. |
| *OVARIAN* | |
| A2780 | −2.3. |
| OVCAR-8 | −2.. |
| OVCAR-5 | −2.6. |
| OVCAR-4 | −2.1. |
| *RENAL* | |
| A498 | −2.. |
| A704 | −1.1. |
| SN-12KI | −2. |
| *PROSTATE* | |
| .AV.LOG IC50 | −1.99 |
| .DELTA | 1.1 |
| .RANGE | 2.5 |

A review of the above data generally confirms that Patellazole A is slightly more active than Patellazole B, which is significantly more active than Patellazole C. Activities of A and B as low as about $10^{-5}$ g/ml have been realized. In Tables IV, V and VI, an activity expressed as −4.5, for example, can also be expressed as $10^{-4.5}$ μg/ml (micrograms per milliliter).

Tables IV through VI are test results illustrating activities against standard cell lines within the National Cancer Institute protocol.

The cytotoxic and antifungal, antiviral activity of these patellazoles may be principally due to the pendant thiazole-epoxide group. Other macrolides wherein the bulk of the compounds may be composed of hydrocarbon rings and side chains which contain a similar thiazole-epoxy group would be expected to have similar chemical and biological properties.

These patellazoles may be admixed with carriers, other active materials and the like, inert materials and the like to form therapeutic compositions or mixtures.

The patellazoles of this invention are further useful inasmuch as the pendant epoxide may be converted to a double bond by removal of the epoxide oxygen or into a diol by hydrolyzing the epoxide.

What is claimed is:

1. A therapeutic mixture comprising a substantially pure patellazole having the following structure:

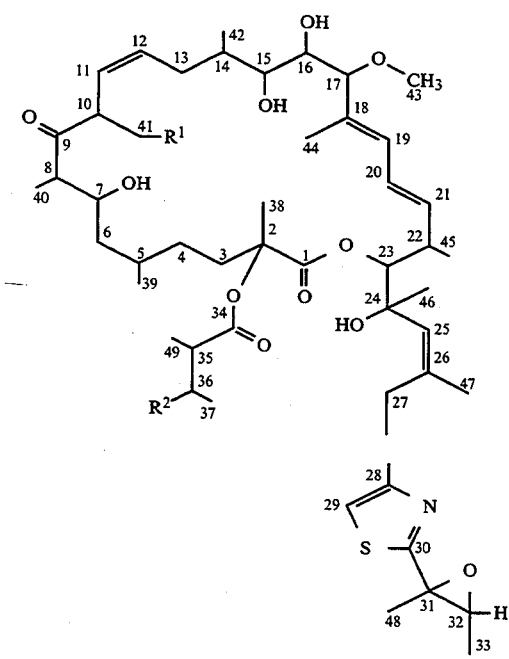

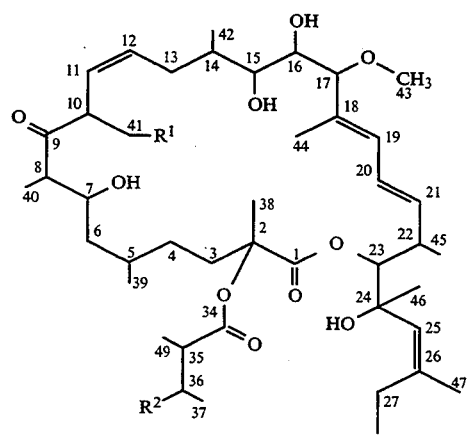

wherein $R_1$ and $R_2$ are either hydrogen or a hydroxyl group.

2. A chemical composition containing a therapeutic amount of a substantially pure patellazole having the following structure:

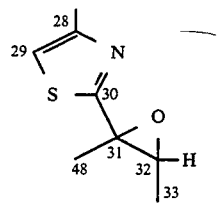

wherein $R_1$ and $R_2$ are either hydrogen or a hydroxyl group.

3. A chemical composition containing a therapeutic agent consisting essentially of a substantially pure patellazole having the following structure:

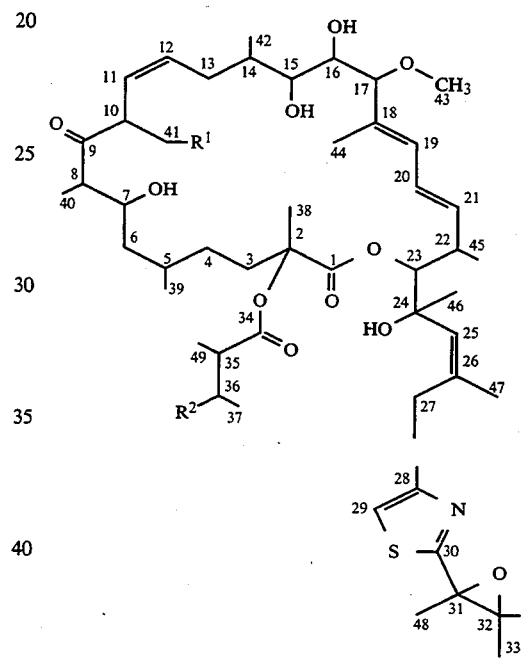

wherein $R_1$ and $R_2$ are either hydrogen or a hydroxyl group.

4. A process for producing a cytotoxic macrolide having the structure:

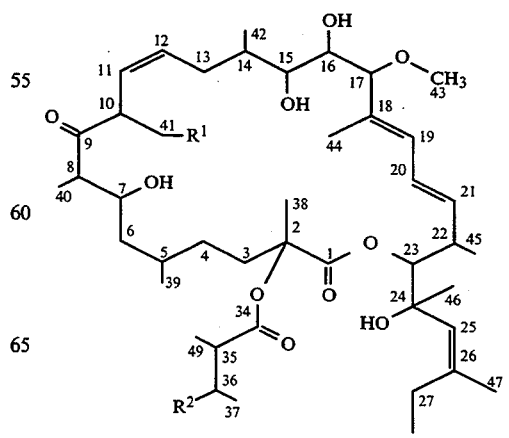

-continued

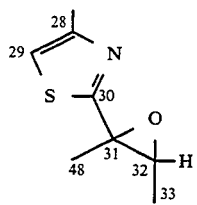

wherein $R_1$ and $R_2$ are either hydrogen or a hydroxyl group, comprising:
a) methyl alcohol (MeOH) extraction of *Lissoclinum patella* collected from the Fiji Islands
b) carbon tetrachloride (CCl$_4$) extraction of the MeOH extract
c) gravity column chromatography of the CCl$_4$ fraction.

5. A process for producing a cytotoxic macrolide composition containing thiazole-containing polyketide metabolites comprising:
a) methyl alcohol (MeOH) extraction of *Lissoclinum patella* collected from the Fiji Islands
b) carbon tetrachloride (CCl$_4$) extraction of the MeOH extract
c) gravity column chromatography of the CCl$_4$ fraction.

6. The therapeutic mixture of claim 1 wherein $R_1$ and $R_2$ are hydrogen.

7. The therapeutic mixture of claim 1 wherein $R_1$ is hydrogen and $R_2$ is a hydroxyl group.

8. The therapeutic mixture of claim 1 wherein $R_1$ and $R_2$ are hydroxyl groups.

* * * * *

UNITED STATES PATENT AND TRADEMARK OFFICE
CERTIFICATE OF CORRECTION

PATENT NO. : 5,405,859
DATED : April 11, 1995
INVENTOR(S) : Chris M. Ireland

It is certified that error appears in the above-indentified patent and that said Letters Patent is hereby corrected as shown below:

In Column 1, line 6, change "CA01779" to --CA01179--.

Signed and Sealed this

Eighteenth Day of July, 1995

Attest:

BRUCE LEHMAN

Attesting Officer  Commissioner of Patents and Trademarks